(12) United States Patent
Moriya

(10) Patent No.: US 8,927,751 B2
(45) Date of Patent: Jan. 6, 2015

(54) HAIR CARE COSMETIC

(75) Inventor: Hiroyuki Moriya, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 136 days.

(21) Appl. No.: 13/323,473

(22) Filed: Dec. 12, 2011

(65) Prior Publication Data
US 2012/0149930 A1 Jun. 14, 2012

(30) Foreign Application Priority Data

Dec. 13, 2010 (JP) ................................ 2010-276572

(51) Int. Cl.
*C07F 7/10* (2006.01)
*A61Q 5/02* (2006.01)
*A61K 8/898* (2006.01)
*A61Q 5/12* (2006.01)

(52) U.S. Cl.
CPC . *A61Q 5/02* (2013.01); *A61K 8/898* (2013.01); *A61Q 5/12* (2013.01)
USPC ........................................................ 556/419

(58) Field of Classification Search
USPC ........................................................ 556/419
See application file for complete search history.

(56) References Cited

U.S. PATENT DOCUMENTS

| 5,756,076 A | 5/1998 | Cervantes et al. |
| 5,976,557 A * | 11/1999 | Friedrich et al. ............... 424/401 |
| 6,124,490 A | 9/2000 | Gormley et al. |

FOREIGN PATENT DOCUMENTS

| JP | 1-190619 A | 7/1989 |
| JP | 9-110653 A | 4/1997 |
| JP | 10-158150 A | 6/1998 |
| JP | 2002-255752 A | 9/2002 |
| JP | 2003-513129 A | 4/2003 |

\* cited by examiner

*Primary Examiner* — Yong Chu
*Assistant Examiner* — Sonya Wright
(74) *Attorney, Agent, or Firm* — Birch, Stewart, Kolasch & Birch, LLP

(57) ABSTRACT

Disclosed herein is a hair care cosmetic which contains an organopolysiloxane defined in following (i) or (ii):

(i) an organopolysiloxane in which the organopolysiloxane segment constituting the backbone has the substituent group represented by the following formula (1) which is connected to at least one silicon atom in the segment;

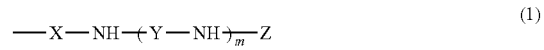

wherein Z is an organic group represented by the following formula (2);

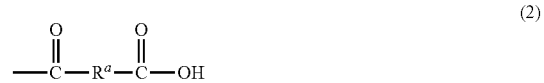

(ii) an organopolysiloxane in which the organopolysiloxane segment constituting the backbone has the substituent group represented by the following formula (1') and the substituent group represented by the following formula (3) which are connected to separate silicon atoms in the segment;

—X—NH—Z (1')

wherein Z is an organic group represented by the following formula (2).

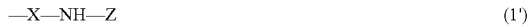

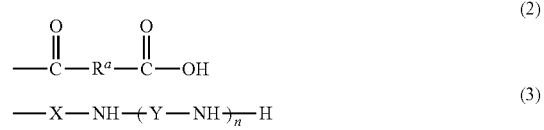

18 Claims, 3 Drawing Sheets

HAIR CARE COSMETIC

CROSS-REFERENCE TO RELATED APPLICATION

This non-provisional application claims priority under 35 U.S.C. §119(a) on Patent Application No. 2010-276572 filed in Japan on Dec. 13, 2010, the entire contents of which are hereby incorporated by reference.

TECHNICAL FIELD

The present invention relates to a hair care cosmetic such as hair rinse, hair conditioner, and hair treatment.

BACKGROUND ART

It has been a conventional practice to use an organopolysiloxane as the base material to impart water repellency or lubricity to the surface of hair or to protect the surface of hair. Especially, an amino-modified organopolysiloxane is known for its ability to adsorb to hair, thereby protecting hair and imparting softness to hair on account of the amino group in its molecule. (See Patent Document 1: JP-A H09-110653, and Patent Document 2: JP-A H01-190619.) Unfortunately, the organopolysiloxane disclosed in these patent documents is not so effective because of its low adsorbability which does not permit it to remain sufficiently on the hair.

It is a known practice to use a carboxamidepolysiloxane as a hair care cosmetic to protect hair from damage caused by permanent wave, hair dyeing, decoloration, and coloration. (See Patent Document 3: JP-A H10-158150, and Patent Document 4: JP-A 2002-255752.) Unfortunately, the disclosed product is poor in adsorption to hair and ability to impart smoothness and moist feeling to hair.

SUMMARY OF THE INVENTION

It is an object of the present invention to provide a hair care cosmetic which, owing to its high adsorbing power, produces such conditioning effects as protecting hair and imparting smoothness, combability, softness, and luster to hair.

As the result of extensive researches to achieve the foregoing object, the present inventor found that an organopolysiloxane having a specific organic group which is composed of a secondary amino group and a carboxyl group, with the amide linkage functioning as a spacer, or which is composed of a primary amino group and an amide carboxyl group exhibits good adsorption to damaged hair and effective hair protection, more specifically, imparts smoothness, softness, and combability to wet hair and to impart smoothness, softness, combability, and luster to dry hair. This finding led to the present invention.

The present invention covers a hair care cosmetic defined as following and a method for production of an organopolysiloxane contained in the hair care cosmetic.

[1] A hair care cosmetic comprising an organopolysiloxane defined in following (i) or (ii).

(i) an organopolysiloxane in which the organopolysiloxane segment constituting the backbone has the substituent group represented by the following formula (1) which is connected to at least one silicon atom in the segment.

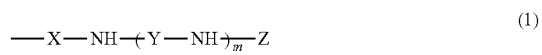

wherein X and Y each independently is a divalent $C_{1-10}$ hydrocarbon group, m is an integer of 1 to 4, and Z is an organic group represented by the following formula (2).

wherein $R^a$ is a divalent $C_{2-12}$ hydrocarbon group.

(ii) an organopolysiloxane in which the organopolysiloxane segment constituting the backbone has the substituent group represented by the following formula (1') and the substituent group represented by the following formula (3) which are connected to separate silicon atoms in the segment;

wherein X is a divalent hydrocarbon group, and Z is an organic group represented by the following formula (2).

wherein $R^a$ is a divalent $C_{2-12}$ hydrocarbon group;

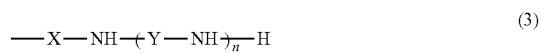

wherein X and Y each independently is a divalent $C_{1-10}$ hydrocarbon group and n is an integer of 0 to 4.

[2] A method for production of an organopolysiloxane defined in (i) or (ii) above, the method comprises reaction between an organopolysiloxane having amino groups and a cyclic acid anhydride.

ADVANTAGEOUS EFFECTS OF THE INVENTION

The present invention provides a hair care cosmetic capable of effectively protecting hair and imparting smoothness to hair.

DESCRIPTION OF THE EMBODIMENTS

Figure 1:
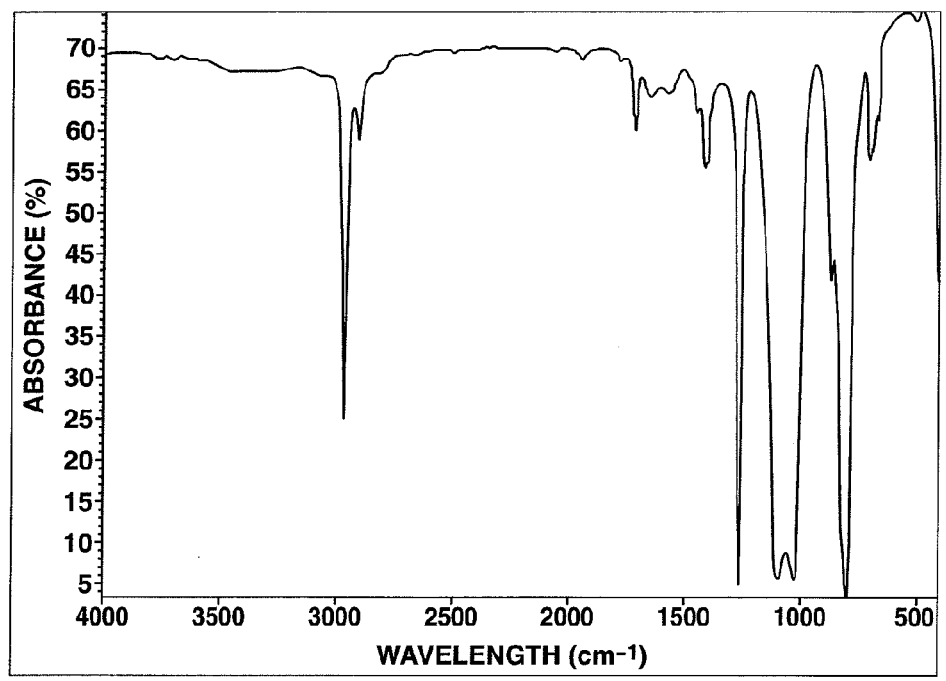
FIG. 1 is an infrared absorption spectrum of the organopolysiloxane synthesized in Preparation Example 1.

The following is a detailed description of the present invention.

The hair care cosmetic according to the present invention contains an organopolysiloxane defined in following (i) or (ii).
(i) An organopolysiloxane in which the organopolysiloxane segment constituting the backbone has the substituent group represented by the following formula (1) which is connected to at least one silicon atom in the segment.
(ii) An organopolysiloxane in which the organopolysiloxane segment constituting the backbone has the substituent group represented by the following formula (1') and the substituent group represented by the following formula (3) which are connected to separate silicon atoms in the segment.

The following description sequentially develops in the order of (I) organopolysiloxane, (II) method for production of the organopolysiloxane, and (III) hair care cosmetic.
(I) Organopolysiloxane
(i) An organopolysiloxane in which the organopolysiloxane segment constituting the backbone has the substituent group represented by the following formula (1) which is connected to at least one silicon atom in the segment.

$$—X—NH{+}Y—NH{\,}_{\overline{m}}Z \qquad (1)$$

wherein X and Y each independently is a divalent $C_{1-1}$ hydrocarbon group, m is an integer of 1 to 4, and Z is an organic group represented by the following formula (2).

$$—\overset{O}{\underset{\|}{C}}—R^a—\overset{O}{\underset{\|}{C}}—OH \qquad (2)$$

wherein $R^a$ is a divalent $C_{2-12}$ hydrocarbon group.

In the formula (1), X and Y each independently is a divalent $C_{1-10}$ hydrocarbon group, which should preferably be a divalent linear or branched $C_{1-10}$ hydrocarbon group, or a divalent $C_{6-10}$ aromatic hydrocarbon group, specifically $C_{1-10}$ or $C_{2-6}$ alkylene groups, alkenylene groups, and phenylene groups, such as ethylene group, ethynylene group, trimethylene group, propylene group, butylene group, isobutylene group, hexamethylene group, and phenylene group; and m is an integer of 1 to 4, preferably 1 to 3.

In the formula (2), $R^a$ is a divalent $C_{2-12}$ hydrocarbon group, preferably a divalent liner or branched aliphatic hydrocarbon group or a divalent $C_{6-10}$ aromatic hydrocarbon group, specifically $C_{1-10}$ or $C_{2-6}$ alkylene groups, alkenylene groups, and phenylene groups, such as ethylene group, ethynylene group, trimethylene group, propylene group, butylene group, isobutylene group, hexamethylene group, and phenylene group.

Incidentally, (i) the organopolysiloxane in which the organopolysiloxane segment constituting the backbone has the substituent group represented by the formula (1) which is connected to at least one silicon atom in the segment may have another substituent group, such as the one represented by the following formula (3), which is connected to a silicon atom different from the silicon atom to which the substituent group represented by the formula (1) is connected.
(ii) An organopolysiloxane in which the organopolysiloxane segment constituting the backbone has the substituent group represented by the following formula (1') and the substituent group represented by the following formula (3) which are connected to separate silicon atoms in the segment.

$$—X—NH—Z \qquad (1')$$

wherein X is a divalent $C_{1-10}$ hydrocarbon group, and Z is an organic group represented by the following formula (2).

$$—\overset{O}{\underset{\|}{C}}—R^a—\overset{O}{\underset{\|}{C}}—OH \qquad (2)$$

wherein $R^a$ is a divalent $C_{2-12}$ hydrocarbon group.

$$—X—NH{+}Y—NH{\,}_{\overline{n}}H \qquad (3)$$

wherein X and Y each independently is a divalent $C_{1-10}$ hydrocarbon group and n is an integer of 0 to 4.

In the formula (1') or (2), X, Z, and $R^a$ are defined by the same examples and ranges as above.

In the formula (3), X and Y each independently is a divalent $C_{1-10}$ hydrocarbon group, which should preferably be a divalent linear or branched $C_{1-10}$ hydrocarbon group, or a divalent $C_{6-10}$ aromatic hydrocarbon group, specifically $C_{1-10}$ or $C_{2-6}$ alkylene groups, alkenylene groups, and phenylene groups, such as ethylene group, ethynylene group, trimethylene group, propylene group, butylene group, hexamethylene group, and phenylene group; and n is an integer of 0 to 4, preferably 0 to 2, more preferably 0.

According to the present invention, the organopolysiloxane defined in Paragraph (i) includes those compounds represented by the following average compositional formula (4).

$$R^{10}{}_a\!-\!\underset{\underset{R}{|}}{\overset{\overset{R_{3-a}}{|}}{Si}}\!-\!O{\left(\!\!\underset{\underset{R}{|}}{\overset{\overset{R^{10}}{|}}{Si}}\!-\!O\!\!\right)}_{\!e}{\left(\!\!\underset{\underset{R}{|}}{\overset{\overset{R}{|}}{Si}}\!-\!O\!\!\right)}_{\!f}{\left(\!\!\underset{\underset{A}{|}}{\overset{\overset{R^{11}}{|}}{Si}}\!-\!O\!\!\right)}_{\!g}{\left(\!\!\underset{\underset{A}{|}}{\overset{\overset{A}{|}}{Si}}\!-\!O\!\!\right)}_{\!h}\!\underset{\underset{R}{|}}{\overset{\overset{R_{3-b}}{|}}{Si}}\!-\!R^{10}{}_b \qquad (4)$$

In the formula (4), R each independently is a hydrogen atom or a group selected from hydroxyl group, $C_{1-3}$ alkoxyl groups, $C_{1-30}$ alkyl groups, fluoroalkyl groups, $C_{6-30}$ aryl groups, and $C_{7-30}$ aralkyl groups. Examples of these groups include alkyl groups such as methyl group, ethyl group, propyl group, butyl group, pentyl group, hexyl group, heptyl group, octyl group, nonyl group, decyl group, stearyl group, cyclopentyl group, and cyclohexyl group; fluoroalkyl groups such as trifluoropropyl group and heptadecafluorodecyl group; aryl groups such as phenyl group and tolyl group; and aralkyl groups such as benzyl group and phenethyl group. Preferable among these groups are $C_{1-15}$ alkyl groups and phenyl groups, more preferably methyl group.

$R^{10}$ is the substituent group represented by the formula (1); $R^{11}$ is an organic group selected from $R^{10}$ and R; and A is the organopolysiloxane segment represented by the following formula (5).

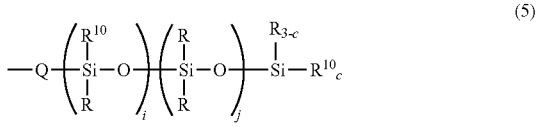

wherein R and $R^{10}$ are defined as above, and Q is an oxygen atom or a divalent $C_{1-3}$ hydrocarbon group.

In the formulas (4) and (5), a, b, and c each independently is an integer of 0 to 3; e is an integer of 0 to 10, preferably 1 to 50; f is an integer of 0 to 5,000, preferably 20 to 200; g is an integer of 0 or 1; h is an integer of 0 or 1; i is an integer of 0 to 100, preferably 1 to 50; and j is an integer of 0 to 5,000, preferably 20 to 2,000, provided that $1 \leq a+b+c+e+g+i$, if $R^{11}$ is $R^{10}$ and $1 \leq a+b+c+e+i$, if $R^{11}$ is R.

According to the present invention, the organopolysiloxane defined in Paragraph (ii) includes those compounds represented by the following average compositional formula (4').

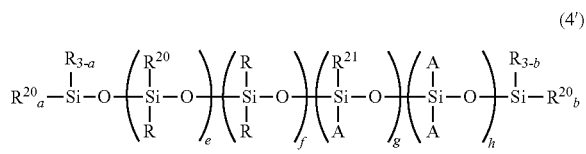

In the formula (4'), R each independently is a hydrogen atom or a group selected from hydroxyl group, $C_{1-3}$ alkoxyl groups, $C_{1-30}$ alkyl groups, $C_{1-30}$ fluoroalkyl groups, $C_{6-30}$ aryl groups, and $C_{7-30}$ aralkyl groups. Examples of these groups include alkyl groups such as methyl group, ethyl group, propyl group, butyl group, pentyl group, hexyl group, heptyl group, octyl group, nonyl group, decyl group, stearyl group, cyclopentyl group and cyclohexyl group; fluoroalkyl groups such as trifluoropropyl group and heptadecafluorodecyl group; aryl groups such as phenyl group and tolyl group; and aralkyl groups such as benzyl group and phenethyl group. Preferable among these groups are $C_{1-15}$ alkyl groups and phenyl groups, more preferably methyl group.

$R^{20}$ is the substituent group represented by the formula (1') or (3), provided that the substituent groups are not connected to the same silicon atom; $R^{21}$ is an organic group selected from $R^{20}$ and R, provided that at least one of $R^{20}$ is a substituent group represented by the formula (1') and at least one of $R^{20}$ is a substituent group represented by the formula (3); and A is the following organopolysiloxane segment represented by the formula (5').

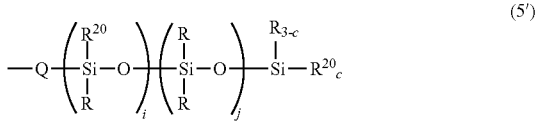

wherein R and $R^{20}$ are defined as above, and Q is an oxygen atom or a divalent $C_{1-3}$ hydrocarbon group.

In the formula (4') and (5'), a, b, and c each independently is an integer of 0 to 3; e is an integer of 0 to 10, preferably 2 to 50; f is an integer of 0 to 5,000, preferably 20 to 2000; g is an integer of 0 or 1; h is an integer of 0 or 1; i is an integer of 0 to 100, preferably 1 to 50; and j is an integer of 0 to 5,000, preferably 20 to 2,000, provided that $2 \leq a+b+c+e+g+i$, if $R^{21}$ is $R^{20}$, and $2 \leq a+b+c+e+i$, if $R^{21}$ is R.

Incidentally, in the formulas (4), (5), (4'), and (5'), a to j are mutually independent.

The organopolysiloxane according to the present invention gives the infrared (IR) absorption spectrum that permits one to know the completion of reaction from the disappearance of peaks attributable to acid anhydride and also know the reaction product from the peak pattern.

(II) Method for Preparing Organopolysiloxane

The organopolysiloxane according to the present invention can be obtained by reaction between an organopolysiloxane having amino groups and a cyclic acid anhydride, which may be at least one species selected from phthalic anhydride, succinic anhydride, glutaric anhydride, and adipic anhydride.

The reaction between an organopolysiloxane having amino groups and a cyclic acid anhydride may be accomplished in any solvent, which includes, without specific restrictions, hydrocarbons such as hexane and toluene, ketones such as acetone and methyl ethyl ketone, amides such as N,N-dimethylacetamide, N,N-dimethylformamide, and N-methyl-2-pyrrolidone, ethers such as tetrahydrofuran and 1,4-dioxane, alcohols such as 2-propanol, and esters such as butyl acetate. Preferable among these solvents are tetrahydrofuran and 1,4-dioxane.

The reaction should be carried out at 30 to 120° C., preferably 60 to 80° C. Reactions at temperatures exceeding 120° C. would bring about cleavage of siloxane chains or side reactions (such as dehydration). The reaction should be continued for one to 20 hours, preferably two to five hours, without specific restrictions.

The organopolysiloxane defined in Paragraph (i) above may be produced by reaction between an amino-modified organopolysiloxane having primary or secondary amines (explained as following) and a cyclic acid anhydride. The amino-modified organopolysiloxane has the amino group represented by the following formula (i) which is connected to at least one silicon atom of the organopolysiloxane segment constituting the backbone.

wherein X and Y each independently is a divalent $C_{1-10}$ hydrocarbon group, and m is an integer of 1 to 4.

The reaction should be accomplished by using the cyclic acid anhydride in an amount sufficient only for reaction with the primary amine. The amount of the cyclic acid anhydride for the primary amine should be less than one equivalent, preferably 0.1 to 1 equivalent. The difference in reactivity between the primary amine and the secondary amine leads to the substituent group represented by the formula (i). For example, in the case where the raw material is dimethylpolysiloxane having five 2-aminoethylaminopropyl groups in one molecule (on average), the amount of the cyclic acid anhydride should be less than 5/5 equivalent for the five amino groups.

The organopolysiloxane defined in Paragraph (ii) above may be produced by reaction between an amino-modified organopolysiloxane having primary amines (explained as following) and a cyclic acid anhydride. The amino-modified organopolysiloxane has the amino group represented by the following formula (ii) which is connected to at least one silicon atom of the organopolysiloxane segment constituting the backbone.

wherein X is a divalent $C_{1-10}$ hydrocarbon group.

In this case, the reaction should be carried out in such a way as to give the product which has at least one substituent group represented by the formulas (1') and (3) in one molecule (on average). To this end, the acid anhydride is reacted with at least one of the two or more primary amino groups in the amino-modified organopolysiloxane used as the starting material. The reaction in this manner yields the organopolysiloxane having both the carboxyl group and the amino group in one molecule, with at least one of the primary amino groups remaining intact. For example, in the case where the raw material is dimethylpolysiloxane having five aminopropyl groups in one molecule (on average), the amount of the cyclic acid anhydride should be 1/5 to 4/5 equivalent for the five amino groups. Likewise, in the case where the raw material is dimethylpolysiloxane having 20 aminopropyl groups in one molecule, the amount of the cyclic acid anhydride should be 1/20 to 19/20 equivalent for the 20 amino groups. Preferably, the amount of the cyclic acid anhydride should be less than 1/2 equivalent.

(III) Hair Care Cosmetic

The hair care cosmetic according to the present invention contains the organopolysiloxane which is produced by the above-mentioned method.

The organopolysiloxane should preferably be contained in an amount of 1 to 20%, more preferably 1 to 10%, and further preferably 1 to 5%, in the hair care cosmetic so that it produces the good long-lasting conditioning effect. ("%" means "% by weight" hereinafter.)

The hair care cosmetic according to the present invention may be incorporated with one or more additional components as listed following which are commonly used for hair care cosmetics.

Oils, those having conditioning action on hair in particular, may be included. They include oils such as lower alcohols, $C_{12-30}$ saturated or unsaturated alcohols, ethers formed from the alcohols and polyhydric alcohols, esters formed from the alcohols and $C_{1-11}$ fatty acids, $C_{12-30}$ saturated or unsaturated fatty acid, esters formed from the fatty acid and monohydric or polyhydric alcohols, amides formed from the fatty acids and amines, sterols, squalene, phospholipids, glycolipids, animal fats and oils, vegetable fats and oils, and silicones other than the organopolysiloxane of the present invention (which include cyclic, linear, or branched dimethylpolysiloxane, methylpolysiloxane, polysiloxane, alkyl-modified silicone, methylphenylpolysiloxane, and polyether-modified silicone). The content of the oils in the hair care cosmetic should preferably be 0.01 to 30%, more preferably 1 to 25%, and further preferably 3 to 20%.

The hair care cosmetic according to the present invention may be incorporated with optional adjuvants in an amount not harmful to the effect of the present invention. They include thickeners (such as hydroxyethyl cellulose), surface active agents, anionic, amphoteric, cationic, or nonionic polymers, perfumes, pearlescent agents, hair setting polymers, dyes, UV absorbers, antioxidants, and preservatives.

The surface active agents may be selected without specific restriction from those which are commonly used for hair care cosmetics. They include anionic, nonionic, amphoteric, and cationic ones.

The anionic surface active agents typically include the following. Linear or branched alkylbenzene sulfonate, preferably one having $C_{10-16}$ alkyl groups (on average); alkyl or alkenyl ether sulfate, preferably one having linear or branched $C_{10-20}$ alkyl or alkenyl groups (on average) and containing 0.5 to 8 mol (on average) of ethylene oxide, propylene oxide, and butylene oxide added thereto in one molecule, with the molar ratio of ethylene oxide to propylene oxide being from 0.1/9.9 to 9.9/0.1 or the molar ratio of ethylene oxide to butylene oxide being from 0.1/9.9 to 9.9/0.1; alkyl sulfate or alkenyl sulfate, preferably one having $C_{10-20}$ alkyl or alkenyl groups (on average); olefin sulfonate, preferably one having 10 to 20 carbon atoms (on average) in one molecule; alkane sulfonate, preferably one having 10 to 20 carbon atoms (on average) in one molecule; salt of higher fatty acid, preferably that of saturated or unsaturated fatty acid having 10 to 24 carbon atoms (on average) in one molecule; surface active agent of (amido) ethercarboxylic acid type; salt or ester of a-sulfofatty acid, preferably one having $C_{10-20}$ alkyl or alkenyl groups (on average); surface active agent of N-acylaminoacid type, preferably one having $C_{8-24}$ acyl groups and free carboxylic acid residues (such as N-acylsarcosinate and N-acyl-β-alanine); surface active agent of phosphate ester type, preferably that of phosphate monoester or diester type having $C_{8-24}$ alkyl or alkenyl groups or alkylene oxide adducts thereof; surface active agent of sulfosuccinate ester type, preferably that of $C_{8-22}$ higher alcohol or ethoxylate thereof, or one derived from higher fatty acid amide; polyoxyalkylene fatty acid amide ether sulfate, preferably that of ethoxylate of $C_{8-24}$ linear or branched saturated or unsaturated fatty acid monoethanolamide or diethanolamide; monoglyceride sulfate ester salt, preferably one having $C_{8-24}$ linear or branched saturated or unsaturated fatty acid groups; acylated isethionate, preferably one having $C_{8-24}$ linear or branched saturated or unsaturated fatty acid groups; alkylglyceryl ether sulfate or alkylglyceryl ether sulfonate, preferably one having $C_{8-24}$ linear or branched alkyl or alkenyl groups or alkylene oxide adducts thereof; alkyl- or alkenylamidosulfonate, preferably one having $C_{8-24}$ linear or branched alkyl or alkenyl groups; alkanolamidosulfosuccinate, preferably one having $C_{8-24}$ linear or branched alkyl group or alkenyl group; alkylsulfoacetate, preferably one having $C_{8-24}$ linear or branched alkyl or alkenyl group; acylated taurate, preferably one having $C_{8-24}$ linear or branched saturated or unsaturated fatty acid groups; and N-acyl-N-carboxyethylglycinate, preferably one having $C_{6-24}$ acyl groups.

The above-mentioned anionic surface active agents should have the base or the counter ion for the anionic residue which is exemplified as following. Alkali metal ion such as sodium and potassium; alkaline earth metal ion such as calcium and magnesium; ammonium ion; and alkanolamine (such as monoethanolamine, diethanolamine, triethanolamine, and triisopropanolamine) having one to three $C_{2-3}$ alkanol groups.

Of the above-mentioned anionic surface active agents, alkyl ether sulfates, especially polyoxyethylene alkyl ether sulfates, are preferable.

The nonionic surface active agents typically include the following. Polyoxyalkylene alkyl ether or polyoxyalkylene alkenyl ether having $C_{10-24}$ linear or branched alkyl or alkenyl groups and ethylene oxide, propylene oxide, or butylene oxide added thereto; glycerin ester of $C_{8-20}$ fatty acid; glycol ester of $C_{8-20}$ fatty acid; alkylene oxide adduct of monoglyceride of $C_{8-20}$ fatty acid; sorbitan ester of $C_{8-20}$ fatty acid; polyglycerin fatty acid ester having $C_{8-20}$ acyl groups; monoethanolamide or diethanolamide or ethoxylate thereof of $C_{8-20}$ fatty acid; polyoxyethylene hardened castor oil; polyoxyalkylene sorbitan fatty acid ester having $C_{8-20}$ acyl groups; polyoxyalkylene sorbit fatty acid ester having $C_{8-20}$ acyl groups; surface active agents of alkyl saccharide type having $C_{8-18}$ linear or branched alkyl, alkenyl, or alkylphenyl groups; alkylamine oxide or alkylamideamine oxide having $C_{8-20}$ linear or branched alkyl or alkenyl groups; ether compound or ester compound of polyhydric alcohol having $C_{8-20}$ linear or branched alkyl or alkenyl groups; polyoxyalkylene-modified organopolysiloxane; polyoxyalkylene-alkyl-co-modified organopolysiloxane, polyglycerin-modified organopolysiloxane, polyglycerin-alkyl-comodified organopolysiloxane, polyoxyalkylene-fluoroalkyl-comodified organopolysiloxane, cross linked polyoxyalkylene-organopolysiloxane, sugar-modified silicone, oxazoline-modified silicone, polyoxyalkylene alkylaryl ether, polyoxyalkylene lanolin alcohol, polyoxyalkylene fatty acid ester, pluronic-type block copolymer, tetronic-type block copolymer, polyoxyalkylene fatty acid amide, polyoxyalkylene alkylamide, and polyethyleneimine derivatives.

The amphoteric surface active agent may be selected without specific restrictions from those which are commonly used for hair care cosmetics. It includes, for example, those of amidoamino acid type, carbobetaine type, amidobetaine type, sulfobetaine type, amidosulfobeaine type, imidazoliumbetaine type, amino acid type, phosphobetaine type, and phosphate ester type.

The cationic surface active agents include tertiary amines, quaternary ammonium salts, amidoamines, and esteramines, which are exemplified as following.

Behenyltrimethylammonium chloride, distearyldimethylammonium chloride, cetyltrimethylammonium chloride, stearyltrimethylammonium chloride, lauryltrimethylammonium chloride, N-stearyl-N,N,N-tri(polyoxyethylene)ammonium chloride (3 mol of ethylene oxide (in total) added), cetylbenzyldimethylammonium chloride, cetyltriethylammonium bromide, distearyldimethylammonium chloride, 2-decyltetradecyltrimethylammonium chloride, 2-dodecylhexadecyltrimethylammonium chloride, di-2-hexyldecyldimethylammonium chloride, di-2-octyldodecyldimethylammonium chloride, behenyl tertiary amine, stearyl tertiary amine, and stearamidopropyldimethylamine.

The content of the surface active agent in the hair care cosmetic should preferably be 0.1 to 50%, more preferably 0.5 to 40%, and further preferably 1 to 30% from the standpoint of foamability.

The hair care cosmetic according to the present invention should preferably be incorporated with any one or more of the compounds listed as following (as the hair setting polymer) if it is intended for use as the hair setting agent, hair foaming agent, or hair spraying agent.

Polyvinylpyrrolidone, polyvinylpyrrolidone-vinyl acetate copolymer, polyvinylpyrrolidone-vinyl acetate-vinyl propionate crosslinked copolymer, polyvinylpyrrolidone-alkylamino acrylate copolymer, polyvinylpyrrolidone-acrylate/(meth)acrylic acid copolymer, and polyvinlpyrrolidone-alkylaminoacrylate-vinylcaprolactum copolymer.

Methyl vinyl ether-maleic anhydride alkyl half ester copolymer.

Vinyl acetate-crotonic acid copolymer, vinyl acetate-crotonic acid-vinyl neodecanoate copolymer, vinyl acetate-crotonic acid-vinyl propionate copolymer, and vinyl acetate-vinyl tert-butylbenzoate-crotonic acid copolymer.

(Meth)acrylic acid-(meth)acrylate ester copolymer and acrylic acid-acrylate alkyl ester-alkylacrylamide copolymer.

(Meth)acrylethylbetaine-(meth)acrylate alkyl ester copolymer, copolymer of N-methacryloyloxyethyl-N,N-dimethylammonium-α-N-methylcarboxybetaine and (meth)acrylate alkyl ester, and acrylate alkyl ester-butylaminoethyl methacrylate-octylamide acrylate copolymer.

Basic acrylic polymeric compounds.

Compounds having the cellulose skeleton and cationic cellulose derivatives.

Hydroxypropylchitosan, carboxymethylchitosan, carboxymethylchitosan, and a salt of chitosan and a monobasic acid (such as pyrrolidonecarboxylic acid, lactic acid, and glycolic acid) or dibasic acid (such as adipic acid and succinic acid).

The content of the hair setting polymer in the hair care cosmetic should preferably be 0.1 to 10%, more preferably 0.5 to 6%, and further preferably 1 to 4%, from the standpoint of necessary and sufficient setting performance.

The hair care cosmetic of the present invention should preferably have a pH value of 2.5 to 9.0, more preferably 3.0 to 5.5, depending on the type of cosmetic. The pH value is that of an aqueous solution diluted 20 times (by weight) which is measured at 25° C.

The hair care cosmetic of the present invention may be hair shampoo, hair treatment, and hair conditioner (to be used in a bathroom), hair foam, hair spray, hair cream, hair wax, and hair gel (to be used outside a bathroom), hair dye, permanent, hair manicure, and hair bleach (to be used in home and beauty salon). All of them may be incorporated with the organopolysiloxane compound according to the present invention. They are suitable for use as hair treatment and hair conditioner because of their good hair protecting effect. They produce their remarkable effect when applied to hair damaged by bleaching.

EXAMPLES

The invention will be described in more detail as following with reference to Preparation Examples, Comparative Preparation Examples, Examples, and Comparative Examples, which are not intended to restrict the scope thereof. Incidentally, the amount of each component shown in the table is expressed in terms of pure product.

Preparation Example 1

A reaction vessel was charged with 500 parts by weight of amino-modified organopolysiloxane represented by the following average compositional formula,

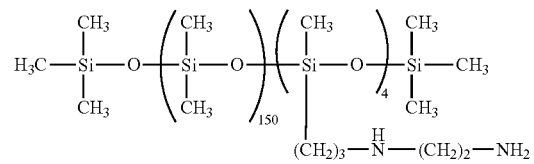

having a viscosity of 320 mm²/s at 25° C. and an amine equivalent of 1,470 g/mol, 100 parts by weight of tetrahydrofuran, and 17 parts by weight of succinic anhydride powder. The reactants were stirred at 50° C. for three hours. The resulting reaction mixture was freed of solvent by evaporation at 90° C. under reduced pressure. Thus there was obtained a colorless clear gum-like liquid (which gave a 30% toluene solution having a viscosity of 14 Pa·s at 25° C.). This product gave an infrared absorption spectrum in which the absorption peaks at 1788 and 1865 cm$^{-1}$ attributable to succinic anhydride are absent and a new absorption peak at 1712 cm$^{-1}$ is present. The infrared absorption spectrum is shown in FIG. 1. This spectrum suggests the structure represented by the following formula.

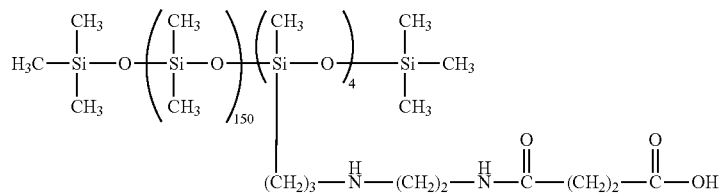

Preparation Example 2

Figure 2:
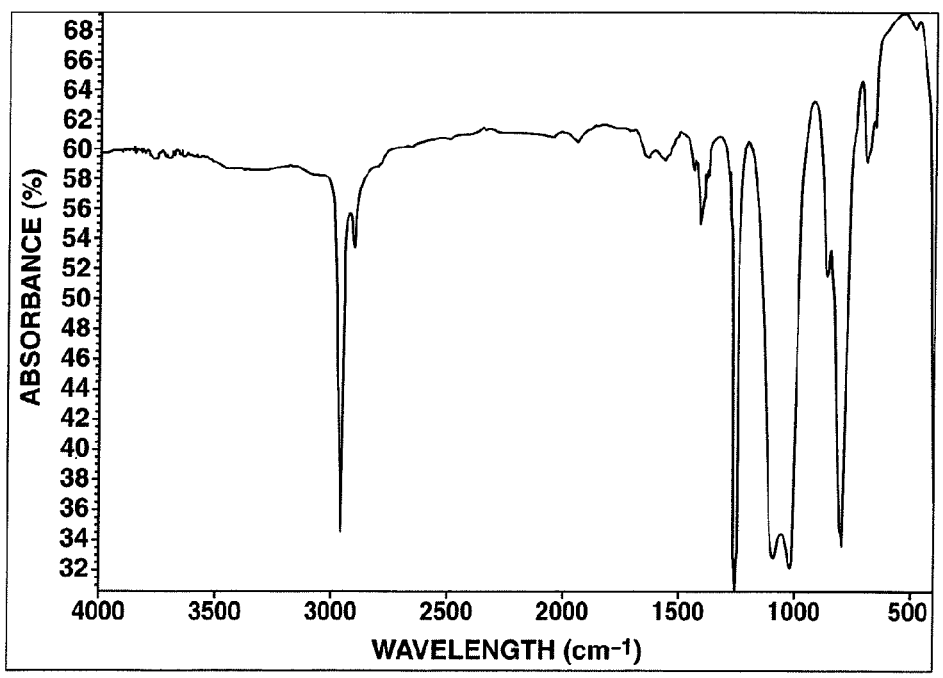
FIG. 2 is an infrared absorption spectrum of the organopolysiloxane synthesized in Preparation Example 2.

A reaction vessel was charged with 500 parts by weight of amino-modified organopolysiloxane represented by the following average compositional formula,

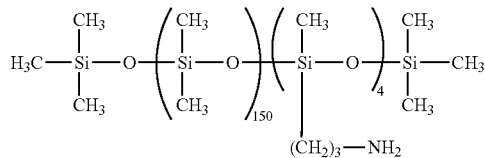

having a viscosity of 320 mm²/s at 25° C. and an amine equivalent of 2,930 g/mol, 100 parts by weight of tetrahydrofuran, and 8.5 parts by weight of succinic anhydride powder. The reactants were stirred at 50° C. for three hours. The resulting reaction mixture was freed of solvent by evaporation at 90° C. under reduced pressure. Thus there was obtained a colorless clear gum-like liquid (which gave a 30% toluene solution having a viscosity of 7.3 Pa·s at 25° C.). This product gave an infrared absorption spectrum in which the absorption peaks at 1788 and 1865 cm$^{-1}$ attributable to succinic anhydride are absent and a new absorption peak at 1642 cm$^{-1}$ is present. The infrared absorption spectrum is shown in FIG. 2. This spectrum suggests the structure represented by the following formula.

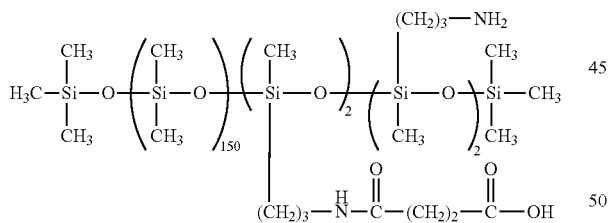

Preparation Example 3

Figure 3:
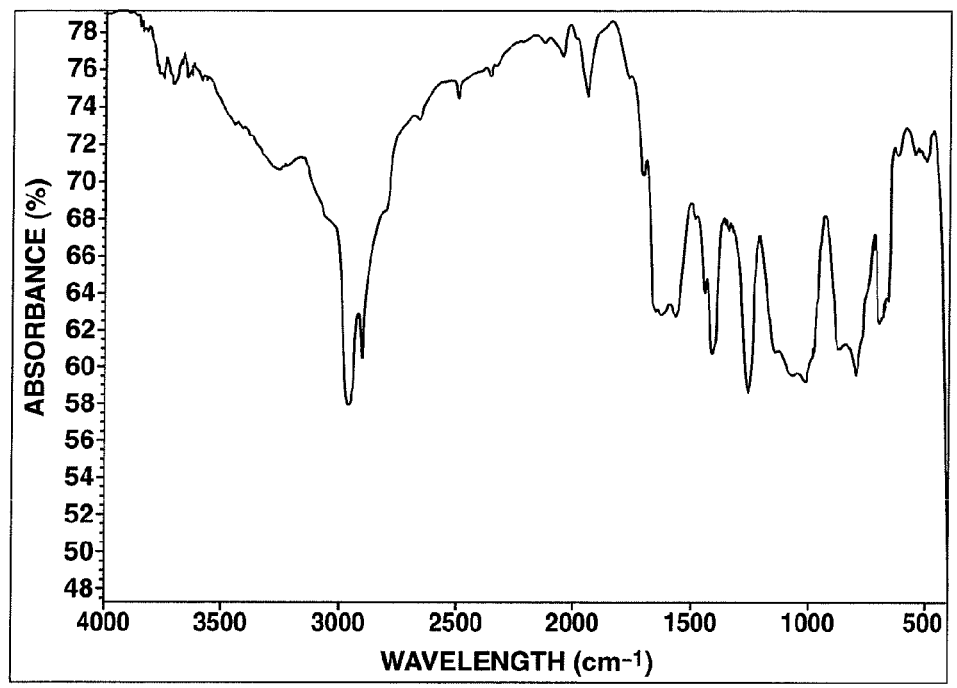
FIG. 3 is an infrared absorption spectrum of the organopolysiloxane synthesized in Preparation Example 3.

A reaction vessel was charged with 300 parts by weight of amino-modified organopolysiloxane represented by the following average compositional formula,

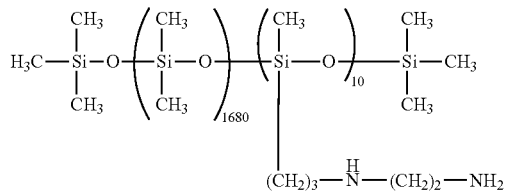

having a viscosity of 60 Pa·s at 25° C. and an amine equivalent of 6,300 g/mol, 40 parts by weight of 2-propanol, and 2.3 parts by weight of maleic anhydride powder. The reactants were stirred at 50° C. for five hours. The resulting reaction mixture was freed of solvent by evaporation at 90° C. under reduced pressure. Thus there was obtained a light yellowish clear gum-like liquid (which gave a 30% toluene solution having a viscosity of 72 Pa·s at 25° C.). This product gave an infrared absorption spectrum in which the absorption peaks at 1780 and 1850 cm$^{-1}$ attributable to maleic anhydride are absent and a new absorption peak at 1633 cm$^{-1}$ is present. The infrared absorption spectrum is shown in FIG. 3. This spectrum suggests the structure represented by the following formula.

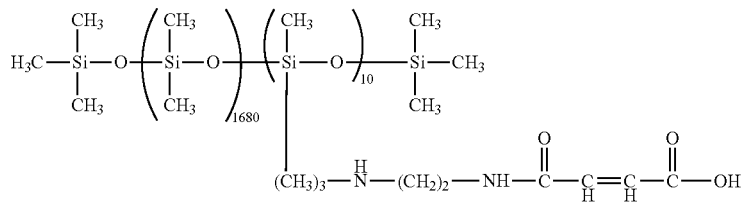

Preparation Example 4

Figure 4:
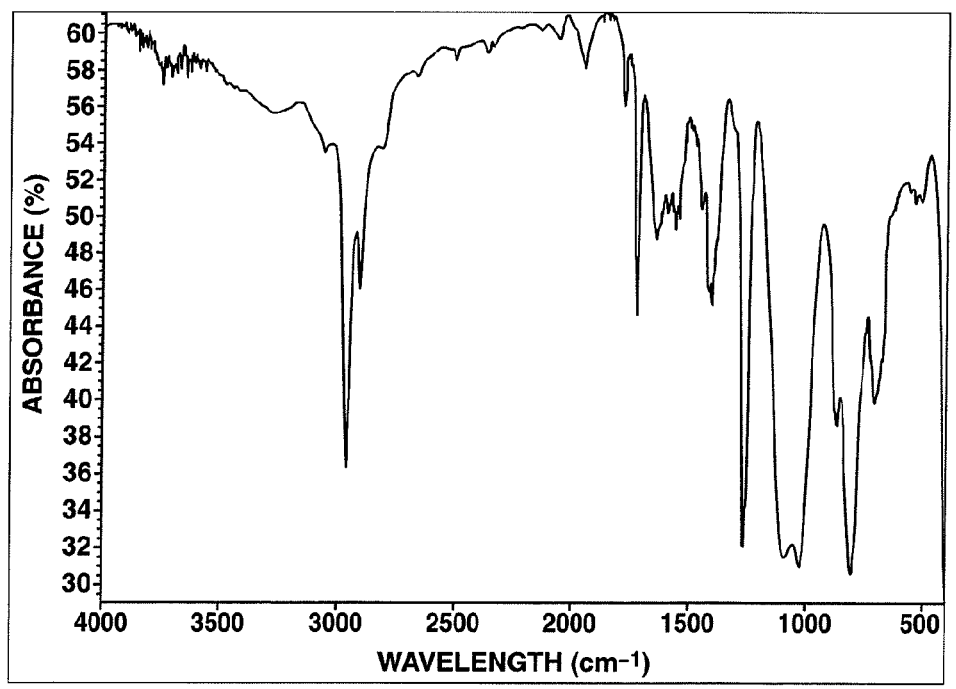
FIG. 4 is an infrared absorption spectrum of the organopolysiloxane synthesized in Preparation Example 4.

A reaction vessel was charged with 300 parts by weight of amino-modified organopolysiloxane represented by the following average compositional formula,

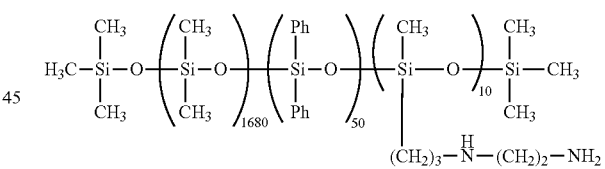

having a viscosity of 82 Pa·s at 25° C. and an amine equivalent of 3,020 g/mol, and 7.3 parts by weight of phthalic anhydride. The reactants were stirred at 80° C. for five hours. Thus there was obtained a light yellowish clear gum-like liquid (which gave a 30% toluene solution having a viscosity of 75 Pa·s at 25° C.). This product gave an infrared absorption spectrum in which the absorption peaks at 1715 and 1853 cm$^{-1}$ attributable to phthalic anhydride are absent and a new absorption peak at 1636 cm$^{-1}$ is present. The infrared absorption spectrum is shown in FIG. 4. This spectrum suggests the structure represented by the following formula.

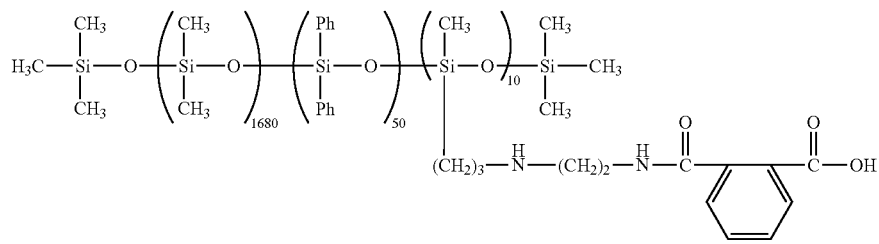

Comparative Preparation Example 1

Figure 5:
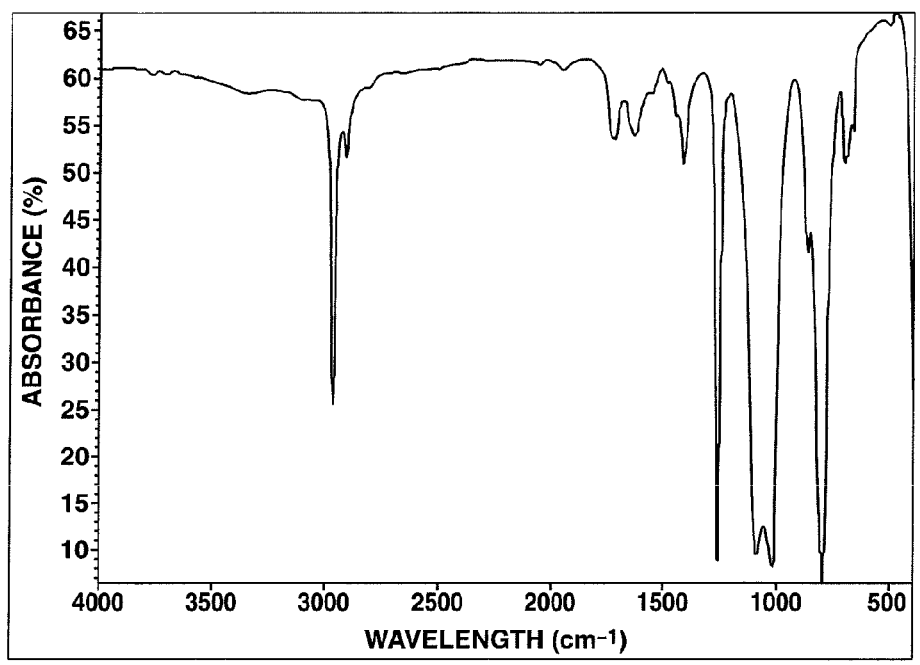
FIG. 5 is an infrared absorption spectrum of the organopolysiloxane synthesized in Comparative Preparation Example 1.

A reaction vessel was charged with 500 parts by weight of amino-modified organopolysiloxane (the same one as shown in Preparation Example 1), 100 parts by weight of tetrahydrofuran, and 34 parts by weight of succinic anhydride powder. The reactants were stirred at 50° C. for three hours. The resulting reaction mixture was freed of solvent by evaporation at 90° C. under reduced pressure. Thus there was obtained a slight yellowish clear gum-like liquid (which gave a 30% toluene solution having a viscosity of 4.0 Pa·s at 25° C.). This product gave an infrared absorption spectrum in which the absorption peaks attributable to succinic anhydride are absent and a new absorption peak at 1713 cm$^{-1}$ is present. The infrared absorption spectrum is shown in FIG. 5. This spectrum suggests the structure represented by the following formula.

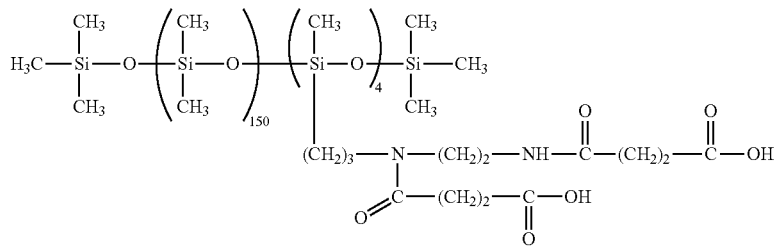

Comparative Preparation Example 2

Figure 6:
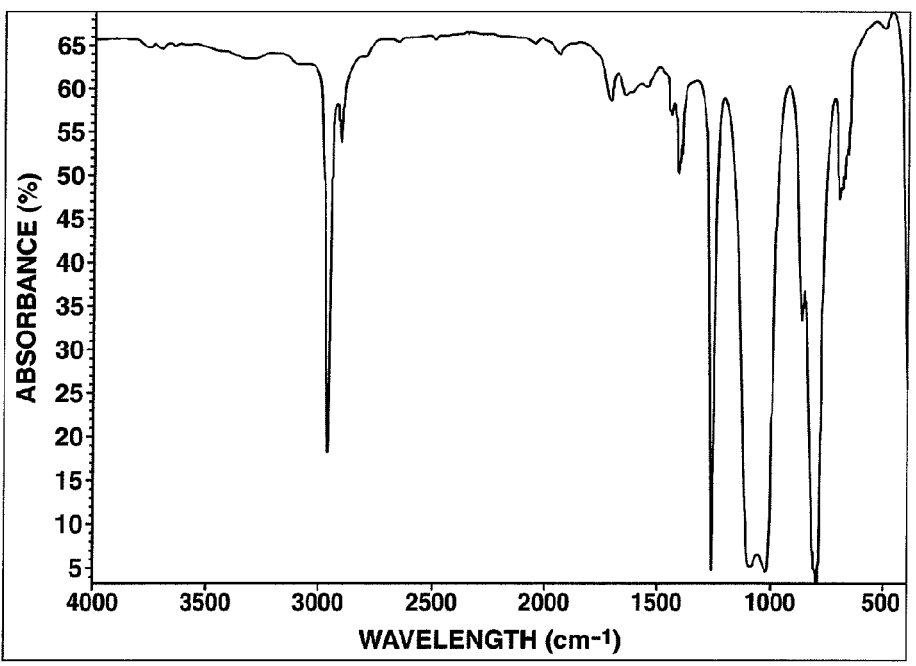
FIG. 6 is an infrared absorption spectrum of the organopolysiloxane synthesized in Comparative Preparation Example 2.

A reaction vessel was charged with 500 parts by weight of amino-modified organopolysiloxane (the same one as shown in Preparation Example 2), 100 parts by weight of tetrahydrofuran, and 17 parts by weight of succinic anhydride powder. The reactants were stirred at 50° C. for three hours. The resulting reaction mixture was freed of solvent by evaporation at 90° C. under reduced pressure. Thus there was obtained a colorless clear gum-like liquid (which gave a 30% toluene solution having a viscosity of 2.3 Pa·s at 25° C.). This product gave an infrared absorption spectrum in which the absorption peaks attributable to succinic anhydride are absent and a new absorption peak at 1650 and 1716 cm$^{-1}$ is present. The infrared absorption spectrum is shown in FIG. 6. This spectrum suggests the structure represented by the following formula.

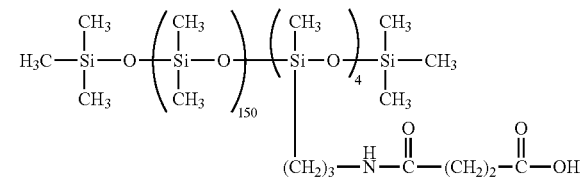

Examples 1 to 4 and Comparative Examples 1 to 5

Samples of the hair conditioner of the present invention were prepared in the usual way according to the recite shown in Table 1 below. The resulting samples underwent organoleptic evaluation in the following way. The results are shown in Table 1 below. Incidentally, the pH values in Table 1 are those of aqueous solutions (diluted 20 times by weight) measured at 25° C.

[Method for Organoleptic Evaluation]

The organoleptic evaluation was performed by five panelists who separately treated a bundle of bleached hairs (20 g, 20 cm) of Japanese female in the following manner. First, the hair bundle was washed with a standard shampoo of the recipe shown below. Then, the washed hair bundle was given 2 g of the hair conditioner specified in Table 1. With the hair conditioner uniformly spread, the hair bundle was rinsed with running water at 40° C. for about 30 seconds. The hair bundle in wet state was evaluated. Finally, the hair bundle was dried with a towel and a drier. The hair bundle in dry state was evaluated. The items for evaluation are as follows.

Smoothness of hair in wet state

Combability and softness of hair in wet state

Smoothness of hair in dry state

Combability and softness of hair in dry state

Luster of hair in dry state

The result of evaluation was rated according to the following criteria in terms of the number of the panelists who answered that the hair conditioner is effective.

| Recipe of standard shampoo (pH 7.0) | |
| --- | --- |
| 25% polyoxyethylene (2.5) lauryl ether sodium sulfate | 62.0% |
| Diethanolamide laurate: | 2.3% |
| Disodium edetate: | 0.15% |
| Sodium benzoate: | 0.5% |
| Sodium chloride: | 0.8% |
| 75% phosphoric acid: | q.s. |
| Perfume: | q.s. |
| Methyl paraben: | q.s. |
| Purified water: | Balance |
| Total | 100.0% |

[Criterion for Rating]

◎: four to five panelists answered "effective"

○: three panelists answered "effective"

Δ: two panelists answered "effective"

X: one or no panelist answered "effective"

Example 5

A hair treatment was prepared in the usual way according to the following recipe.

| | |
| --- | --- |
| Octadecyloxy(2-hydroxypropyl)dimethylamine | 0.5% |
| Dimethylaminopropylamide stearate | 2.0% |
| Stearyl alcohol | 5.0% |
| Dipropylene glycol | 1.0% |
| Benzyl alcohol | 0.5% |
| Phenoxyethanol | 0.1% |
| Organopolysiloxane obtained in Preparation Example 1 | 2.5% |
| Highly polymerized dimethylpolysiloxane *2 | 0.5% |
| Glycerin | 5.0% |
| Polypropylene glycol | 2.5% |
| Lanolin fatty acid | 0.5% |
| Sunflower oil | 0.5% |
| Lactic acid | 1.5% |
| Perfume | 0.4% |
| Sodium hydroxide | q.s. |
| Deionized water | Balance |
| Total | 100.0% |

*2: KF-96H, 100000 cs (Shin-Etsu Chemical)

TABLE 1

| | | Example | | | | Comparative Example | | | | |
| --- | --- | --- | --- | --- | --- | --- | --- | --- | --- | --- |
| | | 1 | 2 | 3 | 4 | 1 | 2 | 3 | 4 | 5 |
| 1 | Organopolysiloxane obtained in Preparation Example 1 | 2 | | | | | | | | |
| 2 | Organopolysiloxane obtained in Preparation Example 2 | | 2 | | | | | | | |
| 3 | Organopolysiloxane obtained in Preparation Example 3 | | | 2 | | | | | | |
| 4 | Organopolysiloxane obtained in Preparation Example 4 | | | | 2 | | | | | |
| 5 | Organopolysiloxane obtained in Comparative Preparation Example 1 | | | | | 2 | | | | |
| 6 | Organopolysiloxane obtained in Comparative Preparation Example 2 | | | | | | 2 | | | |
| 7 | Amino-modified organopolysiloxane used in Preparation Example 1 | | | | | | | 2 | | |
| 8 | Amino-modified organopolysiloxane used in Preparation Example 3 | | | | | | | | 2 | |
| 9 | Dimethylpolysiloxane*[1] | | | | | | | | | 2 |
| 10 | Stearoxypropyldimethylamine | 1.7 | 1.7 | 1.7 | 1.7 | 1.7 | 1.7 | 1.7 | 1.7 | 1.7 |
| 11 | Behenyltrimethylammonium chloride | 0.2 | 0.2 | 0.2 | 0.2 | 0.2 | 0.2 | 0.2 | 0.2 | 0.2 |
| 12 | Behenylpropyldimethylamine | 0.2 | 0.2 | 0.2 | 0.2 | 0.2 | 0.2 | 0.2 | 0.2 | 0.2 |
| 13 | Stearyl alcohol | 5.6 | 5.6 | 3.6 | 5.6 | 5.6 | 5.6 | 5.6 | 3.6 | 5.6 |
| 14 | Benzyl alcohol | 0.3 | 0.3 | 0.3 | 0.3 | 0.3 | 0.3 | 0.3 | 0.3 | 0.3 |
| 15 | Dipropylene glycol | 5 | 5 | 5 | 5 | 5 | 5 | 5 | 5 | 5 |
| 16 | Lactic acid | 1.35 | 1.35 | 1.35 | 1.35 | 1.35 | 1.35 | 1.35 | 1.35 | 1.35 |
| 17 | Glycolic acid | 0.2 | 0.2 | 0.2 | 0.2 | 0.2 | 0.2 | 0.2 | 0.2 | 0.2 |
| 18 | DL-malic acid | q.s. | q.s. | q.s. | q.s. | q.s. | q.s. | q.s. | q.s. | q.s. |
| 19 | Perfume | q.s. | q.s. | q.s. | q.s. | q.s. | q.s. | q.s. | q.s. | q.s. |
| 20 | Water | bal. | bal. | bal. | bal. | bal. | bal. | bal. | bal. | bal. |
| | Total | 100 | 100 | 100 | 100 | 100 | 100 | 100 | 100 | 100 |
| | pH | 3.2 | 3.2 | 3.2 | 3.2 | 3.2 | 3.2 | 3.2 | 3.2 | 3.2 |
| Rating | Smoothness in wet state | ◎ | ◎ | ○ | ○ | X | X | Δ | Δ | X |
| | Combability in wet state | ◎ | ○ | ◎ | ○ | X | Δ | X | X | X |
| | Softness in wet state | ○ | ◎ | ◎ | ○ | X | X | Δ | Δ | Δ |
| | Smoothness in dry state | ◎ | ◎ | ◎ | ○ | X | X | X | Δ | X |
| | Combability in dry state | ◎ | ○ | ◎ | ○ | X | Δ | Δ | Δ | X |
| | Softness in dry state | ◎ | ◎ | ◎ | ○ | X | X | ○ | ○ | X |
| | Luster in dry state | ◎ | ○ | ○ | ◎ | Δ | Δ | Δ | X | X |

*[1]KF-96H, 100000 cs (Shin-Etsu Chemical)

The resulting hair treatment was good in rinsing smoothness, softness, smoothness in dry state, soft feeling, and combability.

Example 6

A hair treatment (pH 4.0) was prepared in the usual way according to the following recipe.

| | |
|---|---|
| Dimethylbehenamine | 2.0% |
| Behenyltrimethylammonium chloride | 0.3% |
| Stearyl alcohol | 4.5% |
| Behenyl alcohol | 1.5% |
| Isononyl isononanoate | 0.5% |
| Organopolysiloxane obtained in Preparation Example 2 | 2.0% |
| Highly polymerized dimethylpolysiloxane *2 | 1.0% |
| Amino-modified organopolysiloxane *3 | 0.5% |
| Glycolic acid | 0.5% |
| Malic acid | 0.1% |
| Dipropylene glycol | 3.0% |
| Benzyl alcohol | 0.3% |
| Arginine | 0.2% |
| Pantothenyl ethyl ether | 0.1% |
| Hydrolyzed conchiolin solution (dry solids content 3%) | 0.05% |
| "Otaneninjin" extract (dry solids content 3%) (*Panax ginseng* C. A. Meyer) | 0.05% |
| Soybean extract (dry solids content 0.4%) | 0.05% |
| *Eucalyptus* extract (dry solids content 0.2%) | 0.05% |
| *Oryza sativa* (rice) germ oil | 0.05% |
| Perfume | q.s. |
| Methyl paraben | q.s. |
| Purified water | Balance |
| Total | 100.0% |

*2: KF-96H, 100000 cs (Shin-Etsu Chemical)
*3: KF-8004 (Shin-Etsu Chemical)

The resulting hair treatment was good in rinsing smoothness, softness, smoothness in dry state, soft feeling, and combability.

Japanese Patent Application No. 2010-276572 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A hair care cosmetic comprising an organopolysiloxane in which the organopolysiloxane segment constituting the backbone has the substituent group represented by the following formula (1') and the substituent group represented by the following formula (3) which are connected to separate silicon atoms in said segment;

$$—X—NH—Z \quad (1')$$

wherein X is a divalent $C_{1-10}$ hydrocarbon group, and Z is an organic group represented by the following formula (2);

(2)

wherein $R^a$ is divalent $C_{2-12}$ hydrocarbon group;

wherein X and Y each independently is a divalent $C_{1-10}$ hydrocarbon group and n is 0.

2. The hair care cosmetic according to claim 1, wherein the organopolysiloxane is a compound represented by the following average compositional formula

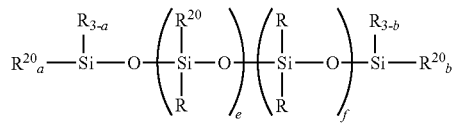

wherein
R is each independently is a hydrogen atom or a group selected from hydroxyl group, $C_{1-3}$ alkoxyl groups, $C_{1-30}$ alkyl groups, $C_{1-30}$ fluoroalkyl groups, $C_{6-30}$ aryl groups, and $C_{7-30}$ aralkyl groups;
$R^{20}$ is the substituent group represented by the formula (1') or (3) as defined above, the substituent groups are not connected to the same silicon atom; at least one of $R^{20}$ is a substituent group represented by the formula (1') and at least one of $R^{20}$ is a substituent group represented by the formula (3);
a and b each independently is an integer of 0 to 3;
e is an integer of 2 to 100; and
f is an integer of 20 to 5,000.

3. The hair care cosmetic according to claim 1, wherein X in the formula (1') is selected from $C_{2-6}$ alkylene groups, $C_{2-6}$ alkenylene groups, and phenylene groups, $R^a$ in the formula (2) is selected from $C_{2-6}$ alkylene groups, $C_{2-6}$ alkenylene groups, and phenylene groups.

4. The hair care cosmetic according to claim 2, wherein X in the formula (1') is selected from $C_{2-6}$ alkylene groups, $C_{2-6}$ alkenylene groups, and phenylene groups, $R^a$ in the formula (2) is selected from $C_{2-6}$ alkylene groups, $C_{2-6}$ alkenylene groups, and phenylene groups.

5. The hair care cosmetic according to claim 2, wherein R in the formula is selected from of $C_{1-15}$ alkyl groups and phenyl groups.

6. The hair care cosmetic according to claim 2, wherein R in the formula is methyl group.

7. The hair care cosmetic according to claim 2, wherein e in the formula is an integer of 2 to 50, and f in the formula is an integer of 20 to 2000.

8. The hair care cosmetic according to claim 1, wherein the organopolysiloxane is compound represented by the average compositional formula (4')

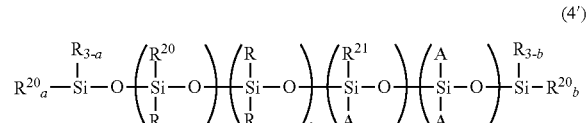

(4')

wherein: R is each independently is a hydrogen atom or a group selected from hydroxyl group, $C_{1-3}$ alkoxyl groups, $C_{1-30}$ alkyl groups, $C_{1-30}$ fluoroalkyl groups, $C_{6-30}$ aryl groups, and $C_{7-30}$ aralkyl groups; $R^{20}$ is the substituent group represented by the formula (1') or (3) as defined in claim 1, and the substituent groups are not connected to the same silicon atom, and $R^{21}$ is an organic group selected from $R^{20}$ and R, wherein at least one $R^{20}$ is a substituent group represented by the formula (1') and at least one $R^{20}$ is a substituent group represented by the formula (3); and A is the organopolysiloxane segment represented by the formula (5')

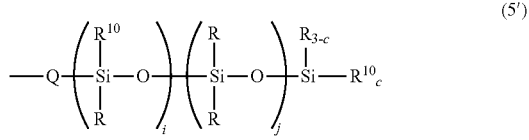

(5')

wherein R and $R^{20}$ are defined as above, and Q is an oxygen atom or a divalent $C_{1-3}$ hydrocarbon group; provided further that in the formulas (4') and (5'), a, b, and c each is 0, e is an integer of 2 to 100, f is an integer of 20 to 5,000, g is an integer of 0 or 1, h is an integer of 0 or 1, i is an integer of 0 to 100, and j is an integer of 0 to 5,000, wherein $2 \leq a+b+c+e+g+i$, if $R^{21}$ is $R^{20}$, and $2 \leq a+b+c+e+i$, if $R^{21}$ is R.

9. The hair care cosmetic according to claim 8, wherein X in the formula (1') is selected from $C_{2-6}$ alkylene groups, $C_{2-6}$ alkenylene groups, and phenylene groups, $R^a$ in the formula (2) is selected from $C_{2-6}$ alkylene groups, $C_{2-6}$ alkenylene groups, and phenylene groups.

10. The hair care cosmetic according to claim 8, wherein R in the formula (4') and formula (5') is selected from $C_{1-15}$ alkyl groups and phenyl groups.

11. The hair care cosmetic according to claim 8, wherein R in the formula (4') and formula (5') is methyl group.

12. The hair care cosmetic according to claim 8, wherein e in the formula (4') is an integer of 2 to 50, and f in the formula (4') is an integer of 20 to 2000.

13. The hair care cosmetic according to claim 1, wherein the organopolysiloxane is compound represented by the average compositional formula (4')

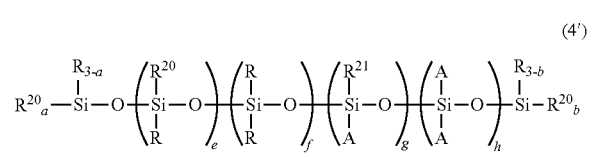

(4')

wherein: R is each independently is a hydrogen atom or a group selected from hydroxyl groups, $C_{1-3}$ alkoxyl groups, $C_{1-30}$ alkyl groups, $C_{1-30}$ fluoroalkyl groups, $C_{6-30}$ aryl groups, and $C_{7-30}$ aralkyl groups; $R^{20}$ is a substituent group represented by the formula (1') or (3) set forth in claim 1, wherein the substituent groups are not connected to the same silicon atom and at least one $R^{20}$ is a substituent group represented by the formula (1') and at least one $R^{20}$ is a substituent group represented by the formula (3); e is an integer of 2 to 100; f is an integer of 20 to 5,000; and each of a, b, g, and h is 0.

14. The hair care cosmetic according to claim 13, wherein X in the formula (1') is selected from $C_{2-6}$ alkylene groups, $C_{2-6}$ alkenylene groups, and phenylene groups, $R^a$ in the formula (2) is selected from $C_{2-6}$ alkylene groups, alkenylene groups, and phenylene groups.

15. The hair care cosmetic according to claim 13, wherein R in the formula (4') is selected from of $C_{1-15}$ alkyl groups and phenyl groups.

16. The hair care cosmetic according to claim 13, wherein R in the formula (4') is methyl group.

17. The hair care cosmetic according to claim 13, wherein e in the formula (4') is an integer of 2 to 50, and f in the formula (4') is an integer of 20 to 2000.

18. The hair care cosmetic according to claim 1, wherein the organopolysiloxane is the compound represented by the formula

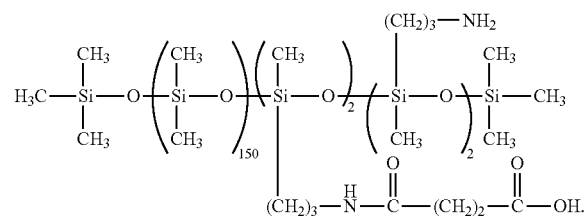

* * * * *